(12) United States Patent
Hyvärinen et al.

(10) Patent No.: US 6,495,831 B1
(45) Date of Patent: Dec. 17, 2002

(54) METHOD AND APPARATUS FOR MEASURING PROPERTIES OF PAPER

(75) Inventors: Timo Hyvärinen, Oulu (FI); Markku Känsäkoski, Kent (GB); Markku Mäntylä, Kangasala (FI); Jussi Tenhunen, Oulu (FI)

(73) Assignee: Metso Paper Automation Oy, Tampere (FI)

( * ) Notice: Subject to any disclaimer, the term of this patent is extended or adjusted under 35 U.S.C. 154(b) by 0 days.

(21) Appl. No.: 09/525,073

(22) Filed: Mar. 14, 2000

Related U.S. Application Data

(63) Continuation of application No. PCT/FI98/00723, filed on Sep. 15, 1998.

(30) Foreign Application Priority Data

Sep. 15, 1997 (FI) .................................. 973693

(51) Int. Cl.⁷ .............................................. G01N 21/86
(52) U.S. Cl. ............................ 250/339.07; 250/339.1
(58) Field of Search ....................... 250/339.07, 339.08, 250/339.1, 341.1, 341.8

(56) References Cited

U.S. PATENT DOCUMENTS

| | | |
|---|---|---|
| 3,641,349 A | 2/1972 | Dahlin |
| 4,319,847 A | 3/1982 | Howarth |
| 4,678,325 A | 7/1987 | Lehtikoski et al. |
| 4,733,078 A | 3/1988 | Sturm |
| 4,801,809 A | 1/1989 | Burk et al. |
| 5,250,811 A * | 10/1993 | Lippert et al. .............. 250/339 |
| 5,343,296 A | 8/1994 | Hellstrom |

FOREIGN PATENT DOCUMENTS

WO    WO 96/42010 A1    12/1996

* cited by examiner

Primary Examiner—Georgia Epps
Assistant Examiner—Richard Hanig
(74) Attorney, Agent, or Firm—Alston & Bird LLP

(57) ABSTRACT

The invention relates to a method and an apparatus for measuring the properties of paper from a moving paper web in a paper machine. An infrared beam is directed to the paper web. The infrared beam, passed through or reflected from the paper web, is split into wavelength components with a spectrograph, and signals of the different wavelength components are measured, and the properties of paper are determined on the basis of the signals.

13 Claims, 1 Drawing Sheet

METHOD AND APPARATUS FOR MEASURING PROPERTIES OF PAPER

CROSS-REFERENCE TO RELATED APPLICATIONS

This application is a continuation of pending PCT International Application PCT/FI98/00723, filed Sep. 15, 1998, designating inter alia the United States.

FIELD OF THE INVENTION

The invention relates to methods and apparatus of measuring the properties of paper from a moving paper web in a paper machine, in which measurement is carried out in the infrared region, most preferably in the wavelength range of 1 to 10 $\mu$m.

BACKGROUND OF THE INVENTION

U.S. Pat. No. 4,733,078 discloses an apparatus which directs a radiation beam to a target through a rotating filter wheel driven by a motor, the filters in the filter wheel emitting only a given wavelength of light at a time to the target. The light that has passed through the paper is detected at different wavelengths and the desired content of the substance is determined from the target on the basis of signals thus obtained. The problem in measuring a moving target is that the measurements of different wavelength channels are successive, since each filter illuminates a different point in the target. Before the following filter has had time to revolve in front of the light source, the target to be measured has slightly moved to a different point, and consequently the penetration point is not quite the same. In this case the proportional measurement, based on a reference wavelength, does not remove the gray factor variation caused by scattering, resulting in a significant error in measurements of non-homogenous, moving material, such as paper.

U.S. Pat. No. 3,641,349 discloses an apparatus in which a light beam, having passed through the paper sheet, is split into several parts. Each different part of the beam is detected by a separate detector, in front of which are disposed narrow-band filters, the signals being measured in parallel. Parallel measurement eliminates measuring noise caused by a non-homogenous moving target, but the number of channels is limited in this solution. The solution becomes cumbersome in applications requiring more than four channels, and its optical efficiency declines as the number of channels increases. Furthermore, because of the filters, resolution and central wavelength tolerances are quite bad, complicating the transfer of calibration from one device to another. The filters used also make it difficult to reach a sufficiently narrow band for the right wavelength, e.g. for measuring kaolin. Still further, lead sulphide detectors are extremely dependent on temperature, a different temperature in detectors disposed at different points causing significant errors in measurement.

WO 96/42010 discloses an apparatus for measuring the color and color-related properties of a moving web by reflectance measurements. This color measurement utilizes a black and white background behind the web, the reflected light beams being measured by two different sensors. The sensor uses a spectrograph which distributes the light beam to the detectors. The measured signals are transmitted serially from the detectors to a computer for further processing. However, serial processing is not always sufficiently efficient. Moreover, the solution of the publication cannot be utilized in applications in which the properties of paper are to be measured in the infrared region.

SUMMARY OF THE INVENTION

It is an object of the present invention to provide a method and an apparatus which avoid the above drawbacks.

The method of the invention is characterized by directing to the paper web an infrared beam modulated by a chopper, splitting the infrared beam which has passed through the paper web or reflected therefrom by a spectrograph into different wavelength components, measuring signals corresponding to the different wavelengths in parallel, detecting the signals using parallel detection synchronized to the chopper, and processing the signal in parallel and determining the properties of the paper on the basis of the wavelength components determined by the spectrograph.

The apparatus of the invention is characterized by comprising a radiation source for producing an infrared beam, a chopper for modulating the infrared beam, a spectrograph for splitting the infrared beam reflected from or passed through the paper web into different wavelength components, means synchronized to the chopper for parallel detection and processing of the wavelength components, and means for determining the properties of the paper on the basis of the different wavelength components split by the spectrograph.

An essential idea of the invention is to measure the properties of a moving paper web by directing an infrared beam modulated by a chopper to the paper, and splitting the beam which has passed through or reflected from the paper into different wavelengths by means of a spectrograph, measuring signals corresponding to the different wavelengths, detecting the signals using parallel detection synchronized to the chopper, and processing the signal in parallel. It is the idea of a preferred embodiment to split a light beam optically by a spectrograph into different wavelengths and to measure the signals of the different wavelengths from the spectrograph with separate detectors. The idea of another preferred embodiment is that the detectors employed are array detectors.

It is an advantage of the invention that because all measuring channels and reference channels are measured exactly simultaneously, the desired statistical accuracy is promptly reached when a non-homogenous rapidly moving sample is measured. Furthermore, detecting and processing the beam in parallel and continuously allows a narrow electric pass band for detector electronics, improving the signal to noise ratio of the detection and making the detection more immune to ambient light interference. Furthermore, measuring time can be utilized to a hundred percent for each channel, which also improves the signal to noise ratio of the detection. A spectrograph provides a high number of channels, good resolution, low central wavelength tolerances and repeatability of the wavelength scale from one device to another. The solution is also applicable to different numbers of wavelengths and to measurements of a continuous spectrum. A high number of wavelengths allows the effect of a change in sample temperature on the measurement to be compensated for, accurate measurements of binders, measurements of different binders, better immunity to interfering components and widening of the basis weight region of the paper to be measured by the use of different wavelength in different applications. In a device with a better wavelength resolution, reference channels can be brought nearer the measuring channel, resulting in e.g. better immunity to baseline bend. In an array detector the detector elements are in the same hermetic casing and of the same production lot, allowing a better immunity to be achieved to changes in ambient temperature than when several separate detectors are used.

In the present application, in addition to paper, the term "paper" also refers to paperboard.

BRIEF DESCRIPTION OF THE DRAWINGS

The invention will be described in greater detail in the attached drawings, in which.

DETAILED DESCRIPTION OF THE INVENTION

Figure 1:
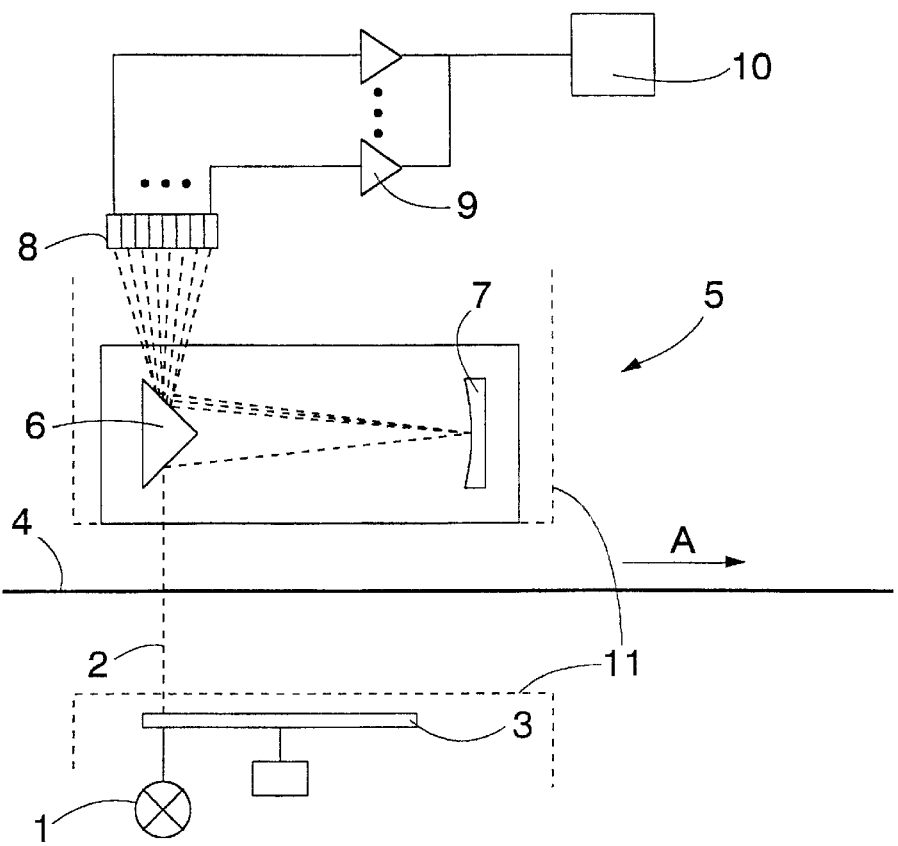
FIG. 1 schematically shows an apparatus of the invention.

The present invention now will be described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout.

The figure shows a radiation source 1 producing an infrared beam 2. A blackbody radiator, for example, can be used as the radiation source. The infrared beam 2 is modulated by a chopper 3 to eliminate the effect of background light, for example, in a manner known per se. The chopper 3 can be e.g. a rotating disc or some other chopper solution known per se. The structure of the chopper 3 is obvious to a person skilled in the art, and is therefore not dealt with in any greater detail herein. After the chopper 3, the infrared beam 2 is directed to a paper web 4 moving on a paper machine. The paper web moves in the direction of arrow A.

The infrared beam 2, passed through the paper web 4, is led to a spectrograph 5. The attached figure shows a spectrograph structure, what is known as a grating spectrograph, in which a mirror 6 and a grate 7 are used to optically split the infrared beam 2 into different wavelength components. A grating spectrograph with no mirror can be used similarly. The different wavelength components from the spectrograph are detected by separate detectors. The wavelength used varies between 1 and 10 $\mu$m and the detection is synchronized to the chopper 3 in a manner known per se. As detectors are preferably used array detectors 8, in which the detector elements are in the same hermetic casing and are of the same production lot, whereby different temperatures cannot affect harmfully the detector elements disposed at different points. The detected signals of different wavelengths are led in parallel from the array detector 8 via a pre-amplifier 9 to a computer 10, where the measured data is processed in a manner known per se. Most preferably the detectors detect a signal using lock-in detection. For the sake of clarity, in addition to the spectrograph 5, the attached figure does not show the optics needed for focusing and directing the infrared beam 2. The structure used to lead/control the beam can be e.g. imaging optics, optic fiber or an optic fiber bundle.

The apparatus is preferably disposed in a measuring frame 11, shown with a dashed line, comprising means for traversing the apparatus transversely with respect to the travel direction A of the web. This way the apparatus does not measure the entire width of the web at the same time, but operates on substantially the entire width of the web as a scanning measuring device.

The spectrograph 5 easily enables e.g. a 24-channel structure, i.e. the infrared beam 2 can be split into 24 different wavelength components. Said technique allows structures with even more channels. An optically splitting spectrograph 5 and an array detector 8 are relatively simple and inexpensive components, making the apparatus of the invention extremely useful.

The computer 10 is used to measure the properties of paper or paperboard, e.g. basis weight with cellulose as the tracer, dry weight of coating with e.g. kaolin, latex or calcium carbonate as the tracer, moisture and/or like magnitudes.

Figure 2:
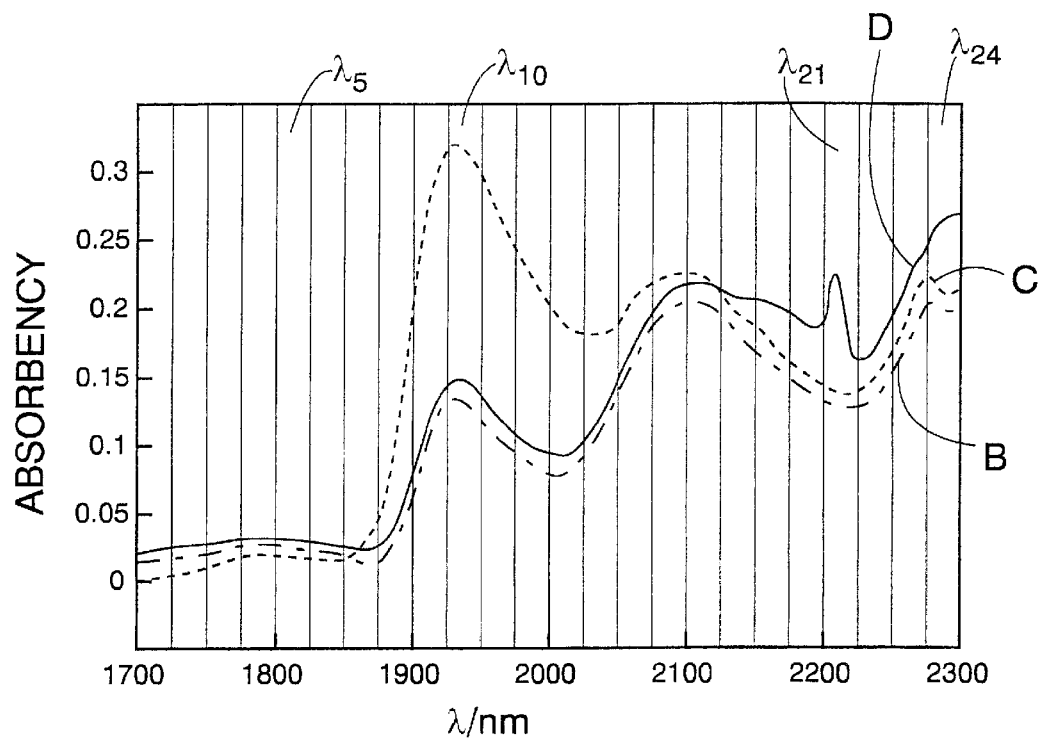
FIG. 2 is a diagram of the spectrum of some paperboard grades.

FIG. 2 shows the spectra of some paperboard grades. The dash-and-dot line shows the spectrum B of paperboard having room, i.e. 5 percent, moisture. The dashed line shows the spectrum C of wet paperboard, i.e. paperboard having a moisture content of 20 percent. The solid line shows the spectrum D of kaolin-coated paperboard. The horizontal axis shows wavelength $\lambda$ as nanometers and the vertical axis shows absorbency. The solution of the invention allows the measuring range of FIG. 2 to be divided into e.g. 24 parts as is shown in FIG. 2. In this case the very narrow kaolin peak at the wavelength range $\lambda_{21}$ can be easily distinguished. At the wavelength range $\lambda_5$ the absorbencies of all qualities are substantially identical, making said wavelength an ideal reference measurement wavelength. Water has an absorption peak at the wavelength range $\lambda_{10}$ shown e.g. in FIG. 2, whereby the amount of water in the paperboard can be determined by measuring the absorption peak of said wavelength. The kaolin peak, in turn, appears at the wavelength range $\lambda_{21}$, that of latex at the wavelength range $\lambda_{24}$, and consequently said tracers are measured at the wavelength ranges $\lambda_2$, and $\lambda_{24}$ of FIG. 2. In other words, the solution of the invention allows simultaneous determination of various paper properties swiftly and accurately, because the measurements at different wavelength ranges can be made simultaneously and because the measurement results are detected and processed in parallel.

The drawing and the related specification are only intended to illustrate the idea of the invention. The details of the invention may vary within the scope of the claims. In other words, the spectrograph may also be arranged to process the different wavelength signals of the light beam by splitting the incoming light beam in an electric form into different wavelength signals, whereby the electric signals can be led directly to separate processing, without any need for separate detectors. Furthermore, the spectrograph can be placed on the same or opposite sides of the paper web with respect to the radiation source, allowing measurement of a light beam that is either reflected from the paper web or has passed through it. However, the solution of the invention provides extremely good results in measurements of a light beam which has passed the paper web even up to a basis weight of 600 g/m$^2$.

Many modifications and other embodiments of the invention will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims.

Although specific terms are employed herein, they are used in a generic and descriptive sense only and not for purposes of limitation.

That which is claimed:

1. A method of measuring the properties of a moving paper web in a paper machine, said method comprising the steps of:

modulating an infrared beam with a chopper;

directing the modulated infrared beam at the paper web;

receiving the infrared beam from the paper web with a spectrograph and splitting the infrared beam into a plurality of different wavelength components;

detecting in parallel the wavelength components split by the spectrograph in synchronization with the chopper;

transmitting signals in parallel that are representative of the detected wavelength components; and, processing in parallel the signals transmitted in parallel to determine properties of the paper on the basis of the different wavelength components split by the spectrograph.

2. A method as claimed in claim 1 wherein said splitting step further comprises optically splitting the infrared beam with the spectrograph into the different wavelength components and said detecting step further comprises detecting the signals of the different wavelength components by detectors.

3. A method as claimed in claim 2 wherein said detecting step comprises detecting the signals using at least one array detector.

4. A method as claimed in claim 2 wherein said detecting step comprises detecting the signals using lock-in detection.

5. A method as claimed in claim 2 wherein said optically splitting step further comprises splitting the infrared beam with a grating spectrograph.

6. A method as claimed in claim 1 wherein said processing step further comprises processing signals corresponding to wavelength components that are indicative of at least one of the moisture, basis weight and amount of coating of the paper web.

7. A method as claimed in claim 1 wherein said step of receiving the infrared beam from the paper web comprises receiving the infrared beam after the infrared beam has passed through the paper web.

8. An apparatus for measuring the properties of a moving paper web in a paper machine, said apparatus comprising:

a radiation source for producing an infrared beam;

a chopper for modulating the infrared beam as the infrared beam is directed towards the moving paper web;

a spectrograph for receiving the infrared beam from the paper web and for splitting the infrared beam into a plurality of different wavelength components;

detectors for parallel detection of the wavelength components in synchronization with the chopper; and a processor for receiving signals transmitted in parallel corresponding to the different wavelength components and processing in parallel the signals to determine properties of the paper on the basis of the different wavelength components split by the spectrograph.

9. An apparatus as claimed in claim 8 wherein said spectrograph comprises at least one grate for optically splitting the wavelength components of the infrared beam and wherein said apparatus further comprises a plurality of detectors capable of detecting optically split wavelength components.

10. An apparatus as claimed in claim 9 wherein said detectors further comprise at least one array detector.

11. An apparatus as claimed in claim 9 wherein the detectors are lock-in detectors.

12. An apparatus as claimed in claim 8 wherein said processor is adapted for processing signals corresponding to wavelength components indicative of at least one of the moisture, basis weight and amount of coating of the paper web.

13. An apparatus as claimed in claim 8 wherein the radiation source is positioned adjacent a side of the paper web and the spectrograph is positioned adjacent an opposite side of the paper web so as to receive the infrared beam after it has passed through the paper web.

* * * * *